United States Patent
Shi et al.

(10) Patent No.: US 10,508,253 B2
(45) Date of Patent: Dec. 17, 2019

(54) PROCESS FOR PREPARING POLYUREA MICROCAPSULES WITH IMPROVED DEPOSITION

(71) Applicant: Firmenich SA, Geneva (CH)

(72) Inventors: Lei Shi, Shanghai (CN); Lahoussine Ouali, Geneva (CH); Nicolas Pichon, Villaz (FR)

(73) Assignee: Firmenich SA, Geneva (CH)

( * ) Notice: Subject to any disclaimer, the term of this patent is extended or adjusted under 35 U.S.C. 154(b) by 153 days.

(21) Appl. No.: 15/318,614

(22) PCT Filed: Jun. 11, 2015

(86) PCT No.: PCT/EP2015/063013
§ 371 (c)(1),
(2) Date: Dec. 13, 2016

(87) PCT Pub. No.: WO2015/189309
PCT Pub. Date: Dec. 17, 2015

(65) Prior Publication Data
US 2017/0121649 A1 May 4, 2017

(30) Foreign Application Priority Data
Jun. 13, 2014 (EP) .................................... 14172393

(51) Int. Cl.
| | |
|---|---|
| *C11D 3/50* | (2006.01) |
| *A61K 8/37* | (2006.01) |
| *A61Q 13/00* | (2006.01) |
| *A61K 8/84* | (2006.01) |
| *A61K 8/02* | (2006.01) |
| *A61K 8/11* | (2006.01) |
| *B01J 13/14* | (2006.01) |
| *A61Q 5/02* | (2006.01) |
| *A61Q 5/12* | (2006.01) |

(52) U.S. Cl.
CPC ............ *C11D 3/505* (2013.01); *A61K 8/0275* (2013.01); *A61K 8/11* (2013.01); *A61K 8/37* (2013.01); *A61K 8/84* (2013.01); *A61Q 5/02* (2013.01); *A61Q 5/12* (2013.01); *A61Q 13/00* (2013.01); *B01J 13/14* (2013.01)

(58) Field of Classification Search
None
See application file for complete search history.

(56) References Cited

U.S. PATENT DOCUMENTS

| | | | |
|---|---|---|---|
| 2006/0216509 A1 | 9/2006 | Kleban et al. | |
| 2013/0330292 A1* | 12/2013 | Lei ......................... | A61K 8/11 424/70.17 |
| 2013/0337023 A1* | 12/2013 | Lei ......................... | A61K 8/11 424/401 |

FOREIGN PATENT DOCUMENTS

| | | |
|---|---|---|
| WO | 2009153695 A1 | 12/2009 |
| WO | 2011161229 A1 | 12/2011 |
| WO | 2012107323 A1 | 8/2012 |

OTHER PUBLICATIONS

International Search Report and Written Opinion, application PCT/EP2015/063013, dated Aug. 18, 2015.

* cited by examiner

*Primary Examiner* — Melissa L Fisher
(74) *Attorney, Agent, or Firm* — Armstrong Teasdale LLP

(57) ABSTRACT

The present invention relates to a process for producing perfume- or flavor-containing polyurea microcapsules with improved deposition of encapsulated actives on targeted surfaces such as fiber, hair and skin, which can be used in home or personal care products, as well as to microcapsules obtainable by such a process and consumer products comprising these microcapsules.

14 Claims, No Drawings

PROCESS FOR PREPARING POLYUREA MICROCAPSULES WITH IMPROVED DEPOSITION

This application is a 371 filing of International Patent Application PCT/EP2015/063013 filed 11 Jun. 2015, which claims the benefit of European patent application no. 14172393.2 filed 13 Jun. 2014

TECHNICAL FIELD

The invention relates to the field of delivery systems. More particularly the present invention relates to a process for producing perfume- or flavor-containing microcapsules with improved deposition of encapsulated actives on targeted surfaces such as fiber, hair and skin, which can be used in home or personal care products, as well as to microcapsules obtainable by such a process and consumer products comprising these microcapsules.

PRIOR ART

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner. Polyurea capsules, formed by polymerisation between a polyisocyanate and a polyamine, are well known capsules that are used in a large variety of technical fields, including perfumery.

However such delivery systems may suffer from a poor deposition on the substrate for the treatment of which they are intended to be used, such as textile, skin, hair or other surfaces, in particular in rinse off applications wherein the capsules could be washed off leading to weak sensory perception and poor lastingness Improving the adherence of capsules onto a surface during application is therefore desirable.

A variety of strategies have been described to improve the deposition of microcapsules on various surfaces. One of the most common solutions disclosed is based on the addition of a deposition aid or on the control of the charge of the shell of the capsules. WO2012107323 discloses for example polyurea microcapsules providing improved deposition of perfume on treated surface and which are formed by the reaction between a polyisocyanate with an amino acid and guanazole. WO2009153695 relates to a process using a specific stabilizer in the form of aqueous polymers in specific proportion to form polyurea microcapsules bearing permanent positive charges in a single step. US20060216509 also addresses that same technical problem by disclosing a process for the cationization of polyurea capsules by acidification or alkylation to bear permanent positive charges. Despite those disclosures, there is still a need to find new solutions to this problem and provide delivery systems which combine good retention efficiency of an encapsulated active ingredient and improved deposition of that active on a target surface.

The industry is also facing a well known problem in processes for the preparation of microcapsules which is that of aggregation of said delivery systems among themselves. This phenomenon leads to several drawbacks in particular processing issues during to production due to difficulties to control the size distribution of aggregates and viscosity of the produced slurries. This is also detrimental to the aesthetic value of the consumer product wherein the microcapsule dispersion is used. Aggregation is therefore usually something that needs to be avoided or controlled.

The present invention provides a solution to the above-mentioned problems by using at least partly aggregated microcapsules which demonstrate an improved deposition on target surfaces, while not compromising the processing of such microcapsules.

SUMMARY

The process to prepare microcapsules developed in this invention is well designed to control the aggregation so as to prevent the formation of too large aggregates which can cause production issues and which are visible in the application. Unexpectedly, the use of at least partly aggregated microcapsules according to the invention provides an improvement of the deposition of said microcapsules on target surfaces such as fiber, hair and skin without any inconvenience usually associated with aggregates.

A first object of the invention consists of a process for the preparation of core-shell microcapsules comprising the following steps:

a) dissolving at least one polyisocyanate having at least two isocyanate groups, in a perfume to form an oil phase;

b) dispersing the oil phase obtained in step a) into an aqueous solution comprising an emulsifier to form an oil-in-water emulsion;

c) adding to the oil-in-water emulsion obtained in step b) a polymeric cross-linker bearing amino groups with a molecular weight equal or higher than 2 000 g/mol, preferably higher than 50 000 g/mol followed by a polyamine with a molecular weight below 250 g/mol to form a microcapsule slurry.

A second object of the present application consists of polyurea microcapsules obtainable by the above-mentioned process and characterized in that they are at least partly aggregated.

A third object of the present invention is a perfuming composition comprising a) at least partly aggregated perfume microcapsules as defined above;

b) at least one ingredient selected from the group consisting of a perfumery carrier, a perfuming co-ingredient and mixtures thereof;

c) optionally at least one perfumery adjuvant.

Another object of the present invention is a perfuming consumer product comprising the polyurea microcapsules obtained by process described above.

A last object of the invention is the use of microcapsules as defined above to prolong the release of a fragrance over time.

DETAIL DESCRIPTION OF THE INVENTION

The process of this invention combines the use of a polymeric cross-linker to generate aggregated droplets and provide capsules with a certain level of aggregation, together with that of a polyamine to make an interfacial polymerization and provide core-shell capsules that are at least partly aggregated.

More particularly, the present invention advantageously solves the above-mentioned problems by adding a polymeric cross-linker bearing amino groups with a molecular weight equal or higher than 2 000 g/mol, preferably higher than 50 000 during the process of the preparation of core-shell microcapsules, and more specifically before the addition of a polyamine responsible for the interfacial polymerization of the capsules.

Therefore, a first object of the present invention is a process for the preparation of core-shell microcapsules comprising the following steps:

a) dissolving at least one polyisocyanate having at least two isocyanate groups, in a perfume or flavor to form an oil phase;

b) dispersing the oil phase obtained in step a) into an aqueous solution comprising an emulsifier to form an oil-in-water emulsion;

c) adding to the oil-in-water emulsion obtained in step b) a polymeric cross-linker bearing amino groups with a molecular weight equal or higher than 2 000 g/mol, preferably higher than 50 000 followed by a polyamine with a molecular weight below 250 g/mol to form a microcapsule slurry.

In the process of the invention, a polymeric cross-linker bearing amino groups with a molecular weight equal or higher than 2 000 g/mol, preferably higher than 50 000 acts as a cross-linking reagent. In particular it forms aggregated or surface coated microcapsules through intermolecular forces such as electrostatic interaction, hydrogen bonding and interfacial reactions. The presence of this polymeric cross-linker in the process is essential as it allows providing microcapsules that are at least partly aggregated. The obtained microcapsules unexpectedly show an improved deposition of the active ingredient on target surfaces while showing good stability in application and good perfume or flavor retention. Moreover, the level of aggregation provided by the process of the invention is such that the at least partly aggregated microcapsules are still susceptible of being processed at an industrial scale.

It is essential to the process of the invention that the polymeric cross-linker bearing amino groups at the origin of the generation of aggregated droplets is added before the polyamine that is going to react with the polyisocyanate by interfacial polymerization. The amino groups of the polymeric cross-linker react through interfacial reaction with the isocyanate functional groups of two different droplets to form covalent bonds between drops, which leads to at least partial aggregation.

The polymeric cross-linker bearing amino groups used in the process of the invention has a molecular weight equal or higher than 2 000 g/mol. Preferably, the polymeric cross-linker bearing amino groups has a molecular weight higher than 50 000 g/mol. Even more preferably, the polymeric cross-linker bearing amino groups used in the process of the invention has a molecular weight higher than 200 000 g/mol. Even more preferably, the polymeric cross-linker bearing amino groups used in the process of the invention has a molecular weight comprised between 200 000 g/mol and 800 000 g/mol.

By the term "molecular weight", it is meant, in case of the polymeric cross-linker, the average molecular weight.

According to a particular embodiment, said polymeric cross-linker is a polymeric cross-linker bearing primary amino groups. By the term primary amino groups, it is meant the normal meaning in the art, i.e. primary amine functional groups wherein a nitrogen atom is substituted by two hydrogen atoms and one hydrocarbyl group.

According to a particular embodiment, said polymeric cross-linker bearing amino groups is selected from the group consisting of polyvinylamines such as those sold under the trade name Lupamine® (trademark from BASF and commercially available from BASF), polyethyleimines such as those sold under the trade name Lupasol® (trademark from BASF and commercially available from BASF), polyaminoethylacrylates and mixtures thereof.

More preferably the polymeric cross-linker bearing amino groups is selected from the group consisting of a polyvinylamine and a polyethyleimine.

In a first step of the process according to the invention, at least one polyisocyanate having at least two isocyanate groups is dissolved in a perfume or flavor to form an oil phase.

According to a preferred embodiment, in a first step of the process according to the invention, at least one polyisocyanate having at least two isocyanate groups is dissolved in a perfume to form an oil phase.

By "perfume or flavor" (or also "perfume or flavor oil") it is meant a perfume or flavor that is liquid at about 20° C. and which will be in the core of the core-shell capsules. According to any one of the above embodiments said perfume or flavor oil in which the polyisocyanate is dissolved in step 1) can be a perfuming or flavoring ingredient alone or a mixture of ingredients, in the form of a perfuming or flavoring composition. As a "perfuming or flavoring ingredient" it is meant here a compound, which is used in a perfuming or flavoring preparation or composition to impart a hedonic effect or modulate the odor or taste. In other words such an ingredient, to be considered as being a perfuming or flavoring one, must be able to impart or modify in a positive or pleasant way the odor or taste of a composition, and not just as having an odor or taste. For the purpose of the present invention, malodor counteracting ingredients are also encompassed by the definition of "perfuming ingredients".

The nature and type of the perfuming or flavoring ingredients present in the perfume or flavor oil do not warrant a more detailed description here, which in any case would not be exhaustive, a skilled person in the art being able to select them on the basis of his general knowledge and according to the intended use or application and the desired organoleptic effect sought. In general terms, these perfuming or flavoring ingredients belong to chemical classes as varied as alcohols, aldehydes, ketones, esters, ethers, acetates, nitriles, terpenoids, nitrogenous or sulphurous heterocyclic compounds and essential oils, and said perfuming or flavoring ingredients can be of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery or flavor. It is also understood that said ingredients may also be compounds able to release in a controlled manner various types of perfuming or flavoring compounds, including what is referred to as "pro-perfumes or to pro-flavors".

In case of a perfume, the perfuming ingredient(s) to be encapsulated may be dissolved in a solvent of current use in the perfume industry. Thus, the core of the capsule might be pure perfuming ingredients or a mixture of perfuming ingredients in an adequate hydrophobic solvent. The solvent is preferably not an alcohol. Examples of such solvents are diethyl phthalate, isopropyl myristate, Abalyn® (rosin resins, available from Eastman), benzyl benzoate, ethyl citrate and isoparaffins. Preferably, the perfume oil comprises less than 20% and more preferably less than 10% of solvent, all these percentages being defined by weight relative to the total weight of the perfume. Most preferably, the perfume is essentially free of solvent.

According to a particular embodiment of the invention, the perfume contains less than 10% of its own weight of primary alcohols, less than 15% of its own weight of secondary alcohols and less than 20% of its own weight of tertiary alcohols. Preferably, the perfume does not contain any primary alcohols and contains less than 15% of secondary and tertiary alcohols. Such limited amounts of alcohols have the advantage of reducing the amount of isocyanate functional groups reacting with the perfume.

According to any one of the invention's embodiments, the concentration of perfume is comprised between 10% and 60% by weight, relative to the total weight of the microcapsule slurry.

According to a particular embodiment, the oil phase comprises perfume oil and the polyisocyanate.

According to a particular embodiment, the oil phase consists essentially of the perfume oil and the polyisocyanate.

The at least one polyisocyanate dissolved in the perfume or flavor to form the oil phase can be any type of polyisocyanate comprising at least two isocyanate groups. Preferably it contains at least three isocyanate groups. The polyamine added in step c) of the process will react with those functional groups by interfacial polymerization to form the core-shell structure of the capsules. Following these numbers of functional groups, an optimal reticulation or network of the capsules wall will be achieved, providing microcapsules exhibiting a prolonged slow release of fragrances, as well as an improved stability in the consumer product. Low volatility polyisocyanate molecules are preferred because of their low toxicity.

Preferably, the at least one polyisocyanate is an aliphatic polyisocyanate, an aromatic polyisocyanate or a mixture thereof. When the at least one polyisocyanate is in the form of a mixture of aliphatic and aromatic polyisocyanates, the at least one aliphatic polyisocyanate and the at least one aromatic polyisocyanate are preferably used in a respective molar ratio comprised between 80:20 and 10:90, more preferably between 75:25 and 20:80, even more preferably between 60:40 and 20:80 and most preferably between 60:40 and 30:70. Such molar ratio is defined as the relative ratio of the number of moles of isocyanate groups provided by the at least one aliphatic polyisocyanate and the number of moles of the isocyanate groups provided by the at least one aromatic polyisocyanate.

The term "aromatic polyisocyanate" is meant here as encompassing any polyisocyanate comprising an aromatic moiety. Preferably, it comprises a phenyl, a toluyl, a xylyl, a naphthyl or a diphenyl moiety, more preferably a toluyl or a xylyl moiety. Preferred aromatic polyisocyanates are biurets and polyisocyanurates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N100), among which a biuret of hexamethylene diisocyanate is even more preferred.

Examples of preferred specific mixtures of at least one aliphatic polyisocyanate and of at least one aromatic polyisocyanate are mixtures of a biuret of hexamethylene diisocyanate with a trimethylol propane-adduct of xylylene diisocyanate, mixtures of a biuret of hexamethylene diisocyanate with a polyisocyanurate of toluene diisocyanate and mixtures of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate.

Preferably the at least one polyisocyanate is used in an amount comprised between 1 and 40%, preferably between 2 and 20% by weight, relative to the total weight of oil phase.

In step b) of the process of the present invention, the oil phase is dispersed into an aqueous solution comprising an emulsifier to form an oil-in-water emulsion. The term "emulsion" is meant to designate the fact that the oil phase obtained in step a) is dispersed in an aqueous solution. The term "emulsion" is therefore understood as emulsion or dispersion. The presence of an emulsifier in the aqueous solution allows the stabilization of the oil droplets therein. In the present invention a colloidal stabilizer could be used as emulsifier. The emulsion may be prepared by high shear mixing and adjusted to the desired droplet size. Droplet size may be checked with light scattering measurements or microscopy. This procedure does not require a more detailed description as it is well known to a skilled person in the art.

The emulsifier could be anionic, neutral or cationic. Examples of emulsifiers include polyvinyl alcohol, cellulose derivatives (such as hydroxyethyl cellulose), polyethylene oxide, copolymers of polyethylene oxide and polyethylene or polypropylene oxide, copolymers of acrylamide and acrylic acid or cationic polymers such as for example a cationic copolymer of vinylpyrrolidone and of a quaternized vinylimidazol such as those sold under the trade name Luviquat® (trademark from BASF, commercially available from BASF), anionic surfactants such as sodium dodecyl sulfate or Stepantex® (trademark from Stepan, commercially available from Stepan), non-ionic surfactants such as diblock copolymers of polyethylene oxide and polyethylene or polypropylene oxide. According to a particular embodiment, the emulsifier is polyvinyl alcohol or a cationic polymer, which is a copolymer of vinylpyrrolidone and of a quaternized vinylimidazol, or a mixture thereof. According to another embodiment, the emulsifier is anionic. According to another embodiment, amphiphilic cationic polymers can be used as emulsifier or as co-emulsifier with non-ionic emulsifier to form positively charged capsules.

In a first embodiment of the invention, the pH of the oil-in-water emulsion obtained in step b) is adjusted above 12 before the addition of the polymeric cross-linker bearing amino groups. The pH is adjusted by the addition of a base. The said base may be selected from the group consisting of NaOH and KOH.

In a second embodiment of the invention, the pH of the oil-in-water emulsion obtained in step b) is not modified before the addition of polymeric cross-linker bearing amino groups and is below 12, preferably above 6.

In a third embodiment of the invention, the pH of the oil-in-water emulsion obtained in step b) is adjusted between 12 and 6 before the addition of polymeric cross-linker bearing amino groups and. The pH is adjusted by the addition of a base as mentioned above.

The pH can be adjusted as a function of the level of aggregation required. The higher the pH is, the higher the level of aggregation is.

In step c) of the process of the invention, a polymeric cross-linker bearing amino groups with a molecular weight equal or higher than 2 000 g/mol, preferably higher than 50 000 is added to the emulsion, followed by a polyamine with a molecular weight below 250 g/mol.

Without being bound by theory, it is believed that the polymeric cross-linker bearing amino groups is responsible for the at least partial aggregation of the microcapsules. In particular said polymeric cross-linker acts as a cross-linking reagent and forms aggregated or surface coated droplets through interfacial reactions. On the other hand, the polyamine allows forming the core-shell capsules by reacting with isocyanate functional groups through interfacial polymerization.

According to a preferred embodiment, the polymeric cross-linker bearing amino groups and the emulsifier are used in a weight ration based on dry matter comprised between 0.1 and 10, more preferably between 0.5 and 2.

For the purpose of the present invention, the polyamine may be used alone, or be admixed with glycerine.

Preferably said polyamine is selected from the group consisting of 1,2-diaminopropane, 1,2-diaminoethane, diethylenetriamine, guanidine, water soluble guanidine salts, tris-(2-aminoethyl)amine, N,N,N',N'-tetrakis(3-aminopropyl)-1,4-butanediamine, N,N'-bis(3-aminopropyl)-ethylenediamine and 3,5-diamino-1,2,4-triazole.

More preferably, the polyamine with a molecular weight below 250 g/mol is selected from the group consisting of water-soluble guanidine salts, guanidine, tris-(2-aminoethyl) amine, N,N'-bis(3-aminopropyl)-ethylenediamine, 3,5-diamino-1,2,4-triazole and N,N,N',N'-tetrakis(3-aminopropyl)-1,4-butanediamine. Most preferably it is selected from guanidine, water-soluble guanidine salts, 3,5-diamino-1,2, 4-triazole and N,N'-bis(3-aminopropyl)-ethylenediamine. By "water soluble guanidine salt" it is meant a salt soluble in water and resulting from the reaction of guanidine with an acid. One example of such salts is guanidine carbonate.

The amount of polyamine used is typically adjusted so that, for each mole of isocyanate group dissolved in the perfume or flavor in step a), there is added from 0.5 to 3 moles of amine groups in step c). Preferably, for each mole of isocyanate group dissolved in the perfume or flavor in step a), 1 to 3, more preferably 1 to 2 moles of amine groups are added in step c).

During final polymerization, temperature is typically comprised between 50 and 75° C.

The specific composition of the polyurea wall is key in obtaining microcapsules that are at the fine balance between release and retention so as to achieve satisfactory release of fragrances, once the capsules are placed on textiles or hair, while showing the desired stability in the product base (e.g. counteracts efficiently the extraction of the perfume by the surfactants of the consumer product) and improved deposition thanks to the controlled aggregation. Therefore the selection of the polyamine and of the polyisocyanate, among the ones mentioned above, enables the fine tuning of the properties and stability of the capsules. On the other hand, the addition of the polymeric cross-linker before the addition of the polyamine allows the improvement of the deposition onto different types of surfaces of the microcapsules. In particular the use of a polymeric cross-linker with high molecular weight leads to the formation of covalent bonds between drops of the dispersion obtained in step b) which results in a partly aggregated microcapsule slurry. The degree of aggregation is controlled by selecting the polymeric cross-linker bearing amino groups and/or adjusting the pH of the oil-in-water emulsion obtained in step b) before the addition of the polymeric cross-linker bearing amino groups followed by a polyamine.

In an optional step of the process of the invention, the microcapsules can be isolated from the slurry. In another optional step, the microcapsules slurry can be dried in a generally known manner to form a polyurea microcapsules powder. Any drying method known to a skilled person in the art can be used including, but not limited to fluidized bed or spray-drying tower with co-current or counter current air streams with atomizing devices of different configuration, such as two-fluid nozzles, rotary nozzles or ultrasonic nozzles. In particular the slurry may be spray-dried preferably in the presence of a polymeric carrier material such as polyvinyl acetate, polyvinyl alcohol, dextrines, maltodextrines, glucose syrups, natural or modified starch, vegetable gums, gum acacia, pectins, xanthanes, alginates, carragenans or cellulose derivatives to provide microcapsules in a powder form. A broad range of suitable spray drying configurations is available from companies like GEA-Niro (Denmark).

The microcapsules obtained by the process of any of the above-described embodiments are also an object of the present invention. Therefore the present invention provides microcapsules comprising:

a polyurea wall, which comprises the reaction product of the polymerization between at least one polyisocyanate having at least two isocyanate groups and a polyamine with a molecular weight below 250 g/mol in the presence of a polymeric cross-linker bearing amino groups with a molecular weight equal or higher than 2 000 g/mol, preferably higher than 50 000 g/mol;

an emulsifier; and a core comprising perfume or flavor, said microcapsules being at least partly aggregated. Said at least partly aggregated microcapsules can be characterized by an agglomeration ratio defined as the ratio between the average size of the at least partly aggregated microcapsules to the average droplet size of the emulsion obtained in step b). Said ratio is comprised between 1.1 and 25, preferably between 1.1 and 10. The aggregated microcapsules have a non-spherical shape which results in larger contact area toward the targeted surface. The deposition of non-spherical aggregated microcapsules is improved compared to that of spherical capsules.

According to a prefer embodiment, the present invention provides microcapsules comprising a core comprising perfume; i.e. the microcapsules of the present invention are perfume microcapsules.

What is meant by average droplet size is a number averaged diameter measured with a microscope on an average over 10 to 20 isolated droplets. This method is well known in the art and does not warrant a more detailed description here. A person skilled in the art is able to measure the average droplet size of the emulsion based on his general knowledge. The average size of at least partly aggregated microcapsules is determined using light scattering which is also a well known method in the art to characterize a size distribution. Detail of the both methods are given is the experimental part.

The at least partly aggregated microcapsules of the invention can be advantageously used for the controlled release of the encapsulated perfume or flavor while improving the deposition of said microcapsules on a target surface. This is particularly advantageous in what is commonly referred to as "rinse off" applications which usually suffer from the problem of losing the encapsulated perfume during rinsing and therefore hardly providing any perfume long-lasting. It is therefore particularly appreciated to include these microcapsules as perfuming ingredients in a perfuming composition or in perfumed consumer products.

Therefore, another object of the present invention is a perfuming composition comprising:

i) at least partly aggregated perfume microcapsules as defined above;

ii) at least one ingredient selected from the group consisting of a perfumery carrier, a perfuming co-ingredient and mixtures thereof; and iii) optionally at least one perfumery adjuvant.

By "perfumery carrier" it is meant a material which is practically neutral from a perfumery point of view i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. Other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or to polymers. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualitat, Behr's Verlag GmbH & Co., Hamburg, 1996.

By "perfuming co-ingredient", it is meant an ingredient equivalent to what has been defined above as perfume ingredient.

By "perfumery adjuvant" what is meant here is an ingredient capable of imparting additional added benefit such as a color, a particular light resistance, chemical stability, etc. A detailed description of the nature and type of adjuvant commonly used in perfuming compositions cannot be exhaustive, but it has to be mentioned that said ingredients are well known to a person skilled in the art.

An invention's composition consisting of the invention's perfume microcapsules and at least one perfumery carrier represents a particular embodiment of the invention. The invention's at least partly aggregated microcapsules can be advantageously used in all the fields of modern perfumery, i.e. fine or functional perfumery, to positively impart or modify the odor of a consumer product into which said invention's microcapsules are added. The microcapsules according to the invention advantageously improve the long-lastingness of the perfume in such consumer products thanks to their improved deposition on the targeted surface to which the consumer product is applied. Consequently, another object of the present invention is a perfuming consumer product comprising, as perfuming ingredient, the invention's at least partly aggregated microcapsules or a perfuming composition as defined above.

The invention's microcapsules can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises a functional formulation, as well as optionally additional benefit agents, corresponding to the desired consumer product, e.g. a detergent or an air freshener, and an effective amount of the invention's microcapsules. For the sake of clarity, said perfuming consumer product is a non-edible product.

The nature and type of the constituents of the perfuming consumer product (functional formulation and optionally benefit agents) do not warrant a more detailed description here, which in any case would not be exhaustive, the skilled person being able to select them on the basis of his general knowledge and according to the nature and the desired effect of said product.

Non-limiting examples of suitable perfuming consumer products include a fine perfume, a cologne, an after-shave lotion, a fabric care product, such as a liquid or solid detergent, a fabric softener, a fabric refresher, an ironing water, a paper, or a bleach; a body-care product, such as a hair care product (e.g. a shampoo, a hair conditioner, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent, a pet-care product such as an animal litter, a hygiene product such as a diaper, sanitary napkin, a liner or a wipe.

According to a preferred embodiment, the perfuming consumer products are preferably hair care products (e.g. a shampoo, a hair conditioner, a coloring preparation or a hair spray), and more preferably shampoos or rinse-off conditioners.

The proportions in which the microcapsules according to the invention can be incorporated into the various aforementioned articles or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 5% by weight, or even more, of the invention's microcapsules based on the weight of the composition into which they are incorporated. Concentrations lower than these, such as in the order of 0.01% to 1% by weight, can be used when these invention's microcapsules are incorporated into perfumed articles, percentage being relative to the weight of the article.

The use of the microcapsules according to the invention to prolong the fragrance release from a surface is another object of the present invention.

The invention will now be described in further details by way of the following examples, which should not be considered as limiting the invention. In the examples, unless otherwise specified, the abbreviations have the usual meaning in the art and the temperatures are indicated in degrees centigrade (° C.).

Example 1

Preparation of Core-Shell Microcapsules According to the Invention
General Procedure:

At least one polyisocyanate (e.g. Takenate® D-110N, trademark from Mitsui Chemicals and/or Desmodur® N100, trademark from Bayer) was dissolved in a perfume. The solution was poured into a KL-506 aqueous solution and emulsified for 3 min using an Ultra-Turrax T25 disperser at 13500 rpm to form an Oil-in-Water (O/W) emulsion. This emulsion was stirred at 400 rpm using a mechanical overhead stirrer and optionally, a NaOH aqueous solution (30 weight % in water) was added to adjust the pH. Then, a polymeric cross-linker bearing amino groups—e.g. Lupamin® 9030 (trademark from BASF) was added followed by addition of a solution of polyamine e.g. guanidine carbonate, which was slowly added during 1 h. Once the addition of guanidine carbonate was finished, the reaction temperature was gradually elevated to between 50 and 75° C. during 1 h and was kept at 70° C. for 3 h. Finally, the formed capsule slurry was cooled down to room temperature.

1.1 Capsules A to F with Lupamin® as Polymeric Cross-Linker Bearing Amino Groups Polyurea microcapsules according to the invention (Capsules A to F) were prepared following the general procedure with the following ingredients:

TABLE 1

Composition of Capsules A to F

| Ingredient | Capsules A Amount (wt %) | Capsules B Amount (wt %) | Capsules C Amount (wt %) | Capsules D Amount (wt %) | Capsules E Amount (wt %) | Capsules F Amount (wt %) |
|---|---|---|---|---|---|---|
| Perfume[1] | 29.70 | 29.70 | 29.70 | 29.70 | 29.70 | 29.70 |
| Desmodur® N100[2] | 2.00 | 2.00 | 2.00 | 2.00 | 0 | 0 |
| Takenate® D-110N[3] | 3.24 | 3.24 | 3.24 | 3.24 | 5.12 | 5.12 |
| Guanidine carbonate | 0.88 | 0.88 | 0.88 | 0.88 | 0.88 | 0.88 |
| KL-506[4] | 1.36 | 1.36 | 1.36 | 1.36 | 1.36 | 1.36 |
| Lupamin 9030[5] | 9.00 | 9.00 | 9.00 | 9.00 | 9.00 | 9.00 |
| NaOH | 1.8 | 0.9 | 0.45 | 0 | 1.8 | 0 |
| Water | 52.02 | 52.92 | 53.37 | 53.82 | 52.14 | 53.94 |

[1] Perfuming composition made with the ingredients of Table 1a
[2] Biuret of hexamethylene diisocyanate, origin: Bayer AG, Germany
[3] Trimethylol propane-adduct of xylylene diisocyanate, origin: Mitsui Chemicals, Inc., Japan
[4] Polyvinyl alcohol, origin: Kuraray Specialities Europe GmbH, Germany
[5] Copolymer of vinylformamide/vinylamine with an average molecular weight of 340 000 g/mol, origin: BASF, Germany TABLE 1a Composition of the perfume

| Ingredient | LogP | Amount (wt %) |
|---|---|---|
| Allyl (cyclohexyloxy)-acetate[a] | 2.72 | 1.2 |
| 2,4-Dimethyl-3-cyclohexene-1-carbaldehyde[b] | 2.85 | 1.2 |
| Menthone | 2.87 | 1.7 |
| Hedione®[c] | 2.98 | 5.8 |
| Camphor | 3.04 | 2.9 |
| Eucalyptol | 3.13 | 5.8 |
| Dihydromyrcenol[d] | 3.47 | 11.5 |
| Rose oxide | 3.58 | 0.9 |
| Isobornyl acetate | 3.86 | 11.5 |
| Delta damascone | 4.13 | 0.6 |
| Casrimeran®[e] | 4.31 | 2.3 |
| Terpenyl acetate | 4.34 | 5.8 |
| Lilial®[f] | 4.36 | 17 |
| Linalyl acetate | 4.39 | 2.3 |
| Neobutenone® alpha[g] | 4.45 | 1.2 |
| Dihydromyrcenyl acetate | 4.47 | 2.3 |
| 2-Methylundecanal | 4.67 | 3.5 |
| Iso E Super®[h] | 4.71 | 11.5 |
| Cetalox®[i] | 4.76 | 0.6 |
| Isoraldeine® 70[j] | 4.84 | 2.3 |
| Habanolide®[k] | 4.88 | 4.6 |
| Precyclemone B[l] | 5.18 | 3.5 |
| Total | | 100.0 |

[a] Origin: Symrise, Holzminden, Germany
[b] Origin: Firmenich SA, Geneva, Switzerland
[c] Methyl dihydrojasmonate, origin: Firmenich SA, Geneva, Switzerland
[d] Origin: International Flavors & Fragrances, USA
[e] 1,2,3,5,6,7-Hexahydro-1,2,3,3-pentamethyl-4h-inden-4-one, origin: International Flavors & Fragrances, USA
[f] 3-(4-Tert-butylphenyl)-2-methylpropanal, origin: Givaudan SA, Vernier, Switzerland
[g] 1-(5,5-Dimethyl-1-cyclohexen-1-yl)-4-penten-1-one, origin: Firmenich SA, Geneva, Switzerland
[h] 1-(Octahydro-2,3,8,8-tetramethyl-2-naphtalenyl)-1-ethanone, origin: International Flavors & Fragrances, USA
[i] Dodecahydro-3a,6,6,9a-tetramethyl-naphtho[2,1-b]furan, origin: Firmenich SA, Geneva, Switzerland
[j] 3-Methyl-4-(2,6,6-trimethyl-2cyclohexen-1-yl)-3-buten-2-one, origin: Givaudan SA, Vernier, Switzerland
[k] Pentadecenolide, origin: Firmenich SA, Geneva, Switzerland
[l] 1-Methyl-4-(4-methyl-3-pentenyl)cyclohex-3-ene-1-carboxaldehyde, origin: International Flavors & Fragrances, USA 1.2 Capsules G with No Polymeric Cross-Linker (Control) and Capsules H to L with Lupasol® as Polymeric Cross-Linker Bearing Amino Groups Polyurea microcapsules according to the invention (Capsules H to L) and control capsules with no polymeric cross-linker (Capsules G) were prepared following the general procedure described above with the following ingredients:

TABLE 2

Composition of Capsules G-L

| Ingredient | Capsules G Amount (wt %) | Capsules H Amount (wt %) | Capsules I Amount (wt %) | Capsules J Amount (wt %) | Capsules K Amount (wt %) | Capsules L Amount (wt %) |
|---|---|---|---|---|---|---|
| Perfume[1] | 28.50 | 28.50 | 28.50 | 28.50 | 28.50 | 28.50 |
| Uvinul A Plus[2] | 1.5 | 1.5 | 1.5 | 1.5 | 1.5 | 1.5 |
| Takenate® D-110N[3] | 5.24 | 5.24 | 5.24 | 5.24 | 5.24 | 5.24 |
| Guanidine carbonate | 0.88 | 0.88 | 0.88 | 0.88 | 0.88 | 0.88 |
| KL-506[4] | 1.36 | 1.36 | 1.36 | 1.36 | 1.36 | 1.36 |
| Lupasol® HF[5] | 0.00 | 5.00 | 0.00 | 0.00 | 0.00 | 0.00 |
| Lupasol® PN 50[6] | 0.00 | 0.00 | 5.00 | 0.00 | 0.00 | 0.00 |
| Lupasol® G 35[7] | 0.00 | 0.00 | 0.00 | 5.00 | 0.00 | 0.00 |
| Lupasol® PS[8] | 0.00 | 0.00 | 0.00 | 0.00 | 5.00 | 0.00 |
| Lupasol® WF[9] | 0.00 | 0.00 | 0.00 | 0.00 | 0.00 | 5.00 |

TABLE 2-continued

Composition of Capsules G-L

| Ingredient | Capsules G Amount (wt %) | Capsules H Amount (wt %) | Capsules I Amount (wt %) | Capsules J Amount (wt %) | Capsules K Amount (wt %) | Capsules L Amount (wt %) |
|---|---|---|---|---|---|---|
| NaOH | 0.17 | 0.90 | 0.90 | 0.90 | 0.90 | 0.90 |
| Water | 62.35 | 56.62 | 56.62 | 56.62 | 56.62 | 56.62 |

[1] Perfuming composition having the ingredients of Table 1a
[2] Used as a tracer for the quantification of oil deposition, origin: BASF, Germany
[3] Trimethylol propane-adduct of xylylene diisocyanate, origin: Mitsui Chemicals, Inc., Japan
[4] Polyvinyl alcohol, origin: Kuraray Specialities Europe GmbH, Germany
[5] Polyethyleneimine with an average molecular weight of 25 000 g/mol, origin: BASF, Germany
[6] Polyethyleneimine with an average molecular weight of 1 000 000 g/mol, origin: BASF, Germany
[7] Polyethyleneimine with an average molecular weight of 2 000 g/mol, origin: BASF, Germany
[8] Polyethyleneimine with an average molecular weight of 750 000 g/mol, origin: BASF, Germany
[9] Polyethyleneimine with an average molecular weight of 25 000 g/mol, origin: BASF, Germany 1.3 Agglomeration Ratios of Capsules a to L The size distribution of the emulsion was first controlled by microscope (Carl Zeiss, AxioScop2, ×40) on an average over 10 to 20 isolated droplets. The size distribution of the emulsion and the final capsules dispersion was controlled by Optical Microscopy and Light Scattering (Mastersizer S, Malvern). The results are summarized in Table 3.

TABLE 3

Emulsion droplet size and capsule size of Capsules A to L

| Capsules | pH | Emulsion Droplet size D[4,3], μm | Capsule size, D[4,3], μm | Agglomeration ratio |
|---|---|---|---|---|
| A | 13.2 | 11 | 155.0 | 14.1 |
| B | 12.7 | 11 | 190 | 17.3 |
| C | 12.7 | 11 | 150 | 13.6 |
| D | 6.2 | 11 | 17 | 1.54 |
| E | 12.7 | 11 | 206 | 18.7 |
| F | 6.2 | 11 | 13 | 1.18 |
| G | 8.13 | 10.3 | 12.7 | 1.2 |
| H | 10.8 | 10.1 | 247 | 24.5 |
| I | 9.4 | 9.72 | 67.2 | 6.9 |
| J | 10.9 | 8.06 | 105 | 13.0 |
| K | 10.5 | 10.1 | 11.1 | 1.1 |
| L | 10.7 | 10.2 | 11.5 | 1.1 |

Example 2

Deposition of Capsules According to the Invention 2.1 Quantification of Deposition of Capsules B Applied in a Shower Gel Introduction Cellulose-modified capsules known as having an improved deposition by hydrogen bonding and referred to as "Capsules M" were used for comparison purposes.

Capsule Preparation

To measure the deposition, 0.3 weight % of Acridine were added to the isocyanate and perfume oil phase during the preparation of Capsules B as described in example 1.

Acridine, HPC and 2 g of Takenate® D-110N were dissolved in the perfume. The solution was heated to 70° C. for 1.5 h and cooled to room temperature. Then the rest of Takenate® D-110N was added under stirring. The final solution was poured into the KL-506 aqueous solution and emulsified using an Ultra-Turrax T25 disperser at 11000 rpm for 2 min and 16000 rpm for 3 min to form an O/W emulsion. This emulsion was stirred at 350 rpm using a mechanical overhead stirrer. A NaOH solution (51 weight % in water) was added followed by TEA-Cl solution. Then, a solution of guanidine carbonate was slowly added during 1 h. Once the addition of guanidine carbonate was finished, the reaction temperature was gradually elevated to 50° C. during 0.5 h and was kept at 50° C. for 3 h.

TABLE 4

Composition of Capsules M

| Ingredient | Capsule M Amount (wt %) |
|---|---|
| Perfume[1] | 29.70 |
| Acridine[2] | 0.3 |
| Takenate® D-110N[3] | 7.31 |
| HPC[4] | 0.02 |
| Guanidine carbonate | 1.80 |
| KL-506[5] | 0.2 |
| TEA-Cl[6] | 0.2 |
| NaOH | 0.02 |
| Water | 60.45 |

[1] Perfuming composition having the ingredients of Table 1a
[2] Used as a tracer for the quantification of oil deposition
[3] Trimethylol propane-adduct of xylylene diisocyanate, origin: Mitsui Chemicals, Inc., Japan
[4] Hydroxy Propyl Cellulose, origin: Nisso Chemicals, Japan
[5] Polyvinyl alcohol, origin: Kuraray Specialities Europe GmbH, Germany
[6] Tetraethylammonium chloride, origin: Sigma-Aldrich, Switzerland The deposition of capsules B was compared to the deposition of capsules M from a shower gel of formula described in Table 5.

Quantification of Deposition for Capsules B and M

TABLE 5

Composition of shower gel formulation

| Ingredient | Amount (wt %) |
|---|---|
| Zetesol AO 328 U[1] | 35% |
| Tego Betain F 50[2] | 8% |
| Aculyn™ 38[3] | 6% |
| Sodium Chloride | 0.02% |
| Water | 50.98% |

[1] Sodium C12-C15 Pareth Sulfate, origin: Zschimmer & Schwarz, Germany
[2] Cocamidopropyl Betaine, origin: Goldschmidt AG, Germany
[3] Acrylates/Vinyl Neodecanoate Crosspolymer, origin: Rohm & Haas, USA A hair swatch (500 mg) was wetted with 40 mL of tap water flowing at 36-40° C. Excess water was removed by manually squeezing once. 0.2 mL of unperfumed shower gel was applied along the length of swatch and agitated by fingers. The swatch was rinsed with 100 mL running water and excess water was removed again by squeezing. Then 0.2 mL of shower gel (composition described in Table 5) containing 1.33% by weight of capsules B, respectively M relative to the total weight of the shower gel (i.e. shower gel contained 0.4% perfume) was applied along the length of swatch and agitated by fingers. The swatch was then rinsed with 100 mL running water and excess water was shaken off. The treated part of the swatch was cut into a glass vial and dried at 60-75° C. Three repetitions of swatches were treated for reproducibility. 4 mL of acetonitrile were added to the dry hair and the vial was shaken for 1 h to extract any deposit. The extract was filtered and measured on an HPLC for fluorescence. The efficiency of the deposition of the capsules could be determined by comparing the fluorescence of the extract from treated hair swatch versus that directly from 0.2 mL shower gel containing capsules B or M. The results are shown in Table 6.

TABLE 6

Size and deposition efficiency of capsules B and M

| Sample | Deposition Efficiency[1] |
|---|---|
| Capsules B | 1.3% |
| Capsules M | 0.16% |

[1] Deposition Efficiency = Fluorescence of the acetonitrile extract from treated hair × 100%/Fluorescence of the acetonitrile extract from 0.2 mL perfumed shower gel containing capsules The deposition efficiency of Capsules B (according to the invention) is more than eight times higher than that of Capsules M.

2.2 Quantification of Deposition for Capsules G-L in Shampoo

TABLE 7

Composition of the shampoo formulation

| Ingredient | Amount (wt %) |
|---|---|
| Jaguar C-14S[1] (Rodhia) | 0.4% |
| Dehyton AB-30[2] (Cognis) | 7% |
| Texapon NSO IS[3] (Cognis) | 45.0% |
| Dow Corning 2-1691[4] emulsion | 3% |
| Cutina AGS[5] (Cognis) | 0.9% |
| Rewomid IPP 240[6] (Degussa) | 1.2% |
| Cetyl alcohol | 1.2% |
| Glydant plus liquid[7] (Lonza) | 0.3% |
| Water | 41% |

[1] Guar gum, 2 hydroxy-3-(trimethylammonium)propyl ether chloride, origin: Rhodia, La Défense, France
[2] Coco Betain, origin: Cognis, Monheim am Rhein, North Rhine-Westphalia, Germany
[3] Sodium lauryl ether sulfate + 2EO, origin: Cognis, Monheim am Rhein, North Rhine-Westphalia, Germany
[4] dimethyl(oxo)silane, origin: Dow Corning Corporation, Midland, USA
[5] Ethylene glycol distearate origin: Cognis, Monheim am Rhein, North Rhine-Westphalia, Germany
[6] Cocamide MIPA, origin: Degussa, Essen, Germany
[7] DMDM hydantoin and iodopropynyl butylcarbamate, origin: Lonza A hair swatch (500 mg) was wetted with 40 mL of tap water flowing at 36-40° C. Excess water was removed by manually squeezing once. 0.2 mL of unperfumed shampoo was applied along the length of swatch and agitated by fingers. The swatch was rinsed with 100 mL running water and excess water was removed again by squeezing. Then 0.2 mL of shampoo containing 1.33% by weight of capsules G-L relative to the total weight of the shampoo (i.e. shampoo contained 0.4% perfume) was applied along the length of swatch and agitated by fingers. The swatch was then rinsed with 100 mL running water and excess water was shaken off. The treated part of the swatch was cut into a glass vial and dried at 60-75° C. Three repetitions of swatches were treated for reproducibility. 5 ml of ethanol was added to the dry hair and the vial was shaken for 1 h to extract any deposit. The extract was filtered, concentrated and measured on an HPLC for UV absorption. The efficiency of the deposition of the capsules could be determined by comparing the UV absorption of the extract from treated hair swatch versus that directly from 0.2 mL shampoo containing capsules G-L. The results are shown in Table 8.

TABLE 8

Deposition efficiency of capsules G-L

| Sample | Deposition Efficiency[1] |
|---|---|
| Capsules G | 0.23% |
| Capsules H | 0.93% |
| Capsules I | 0.91% |
| Capsules J | 0.43% |
| Capsules K | 0.99% |
| Capsules L | 0.63% |

[1] Deposition Efficiency = UV absorption of the ethanol extract from treated hair × 100%/UV absorption of the ethanol extract from 0.2 mL perfumed shampoo containing capsules The deposition efficiency of Capsules H, I, and K (according to the invention) is ~4 times higher than that of Control Capsules G. The deposition efficiency of Capsules J (according to the invention) is ~2 times higher than that of Capsules G. The deposition efficiency of Capsules L (according to the invention) is ~3 times higher than that of Capsules G.

Example 3

Hair Shampoo Product Comprising the Capsules of the Invention and Olfactive Evaluation Thereof The olfactive performance of the Capsules A to F from Example 1 was evaluated in the above hair shampoo formulation described in table 7. 0.66% by weight of capsules according to the invention relative to the total weight of the shampoo formulation were respectively dispersed in the shampoo formulation prepared above. A 10 g hair swatch was first washed with 2.5 g of this shampoo formulation containing the capsules, rinsed for 30 seconds under tap water at 37° C. before repeating the same wash/rinse operation a second time. The hair swatch was then left to dry for 6 h at room temperature before evaluating.

The intensity of the perception of the perfume on the hair swatches washed with the above shampoo formulation was evaluated by a panel of 10 trained panelists. They were asked to rate the intensity of the perfume perception on a scale ranging from 1 to 7, wherein 1 means no odour and 7 means very strong odour and then to comb gently the hair swatches 3 times and to rate a second time the intensity of the perfume perception. The results are summarized in the following table.

TABLE 9

Olfactive performance of capsules A to F in a shampoo

| | Fresh Sample | | After 3 months at 45° C. | |
|---|---|---|---|---|
| Shampoo[1] | Before rubbing | After rubbing | Before rubbing | After rubbing |
| Shampoo A | 2.5 | 3.8 | 2.0 | 3.8 |
| Shampoo B | 2.1 | 3.8 | 1.8 | 3.5 |
| Shampoo C | 2.0 | 3.7 | 1.5 | 3.2 |
| Shampoo D | 2.2 | 5.5 | 1.6 | 4 |
| Shampoo E | 2.2 | 3.7 | 1.4 | 3.7 |
| Shampoo F | 2.3 | 4.5 | 1.6 | 4.5 |

[1] Shampoos A to F correspond to the base composition from Table 7 with capsules A to F as described in example 1

The perfume intensity has been evaluated by the panel with all the capsules of the invention as being higher after rubbing than on fresh samples. The rubbing action is mechanically breaking the capsules that did deposit on the hair and remained even after rinsing. This result thus demonstrates the quality of the deposition. Furthermore, the olfactive performance of the invention's capsules in a shampoo was similar with a fresh prepared shampoo base compared to a 3 months old shampoo base which demonstrates the stability of the capsules of the invention in the consumer product.

Example 4

Rinse-Off Hair Conditioner Product Comprising the Capsules of the Invention and Olfactive Evaluation Thereof

TABLE 10

Composition of the Rinse-off hair conditioner formulation

| Ingredient | Amount (% wt) |
|---|---|
| Water | 82.55 |
| Chlorhexidine Dihydrochloride[1] | 0.05 |
| Hydroxyethylcellulose[2] | 1 |
| Cetearyl alcohol (and) Dipalmitoylethyl Hydroxyethylmonium methosulfate (and) Ceteareth-20[3] | 0.2 |
| Amodimethicone (and) Trideceth-6[4] | 1.2 |
| Behentrimonium Chloride[5] | 1 |
| Cetyl Esters[6] | 0.5 |
| Cetyl Alcohol[7] | 3 |
| Alcohol C 14[8] | 0.2 |
| Water | 10 |
| Methylparaben[9] | 0.3 |

[1] Chlorhexidine Dihydrochloride, Sigma-Aldrich, Switzerland
[2] Hydroxyethylcellulose, Ashland, UK
[3] Cetearyl alcohol (and) Dipalmitoylethyl Hydroxyethylmonium methosulfate (and) Ceteareth-20, BASF, Germany
[4] Amodimethicone (and) Trideceth-6, BASF, Germany
[5] Behentrimonium Chloride, Croda, Germany
[6] Cetyl Esters, Lipo Chemicals, USA
[7] Cetyl Alcohol, Sigma-Aldrich, Switzerland
[8] Alcohol C 14, Sigma-Aldrich, Switzerland
[9] Methylparaben, Sigma-Aldrich, Switzerland The olfactive performance of Capsules A to F as described in Example 1 was evaluated in a rinse-off hair-conditioner formulation (Table 10). 0.66% by weight of capsules according to the invention relative to the total weight of the rinse-off hair-conditioner were respectively dispersed in the base. A 10 g hair swatch is first washed with 2.5 g of the shampoo formulation described in example 1 (unperfumed and without capsules), rinsed for 30 seconds under tap water at 37° C. before spreading 0.5 g of above rinse-off hair-conditioner formulation with capsules. The hair swatches were left to dry for 6 h at room temperature before evaluating.

The intensity of the perception of the perfume on the hair swatches treated with the above rinse-off hair conditioner formulation with capsules was evaluated by a panel of 10 trained panelists. They were asked to rate the intensity of the perfume on a scale ranging from 1 to 7, wherein 1 means no odour and 7 means very strong odour and then to comb gently the hair swatches 3 times and to rate a second time the intensity of the perfume perception. The results are summarized in the following table.

TABLE 11

Olfactive performance of capsules A to F in a rinse-off hair conditioner

| Conditioner[1] | Fresh Sample | | After 3 months at 45° C. | |
|---|---|---|---|---|
| | Before rubbing | After rubbing | Before rubbing | After rubbing |
| Conditioner A | 3.1 | 5.5 | 2.4 | 4.0 |
| Conditioner B | 2.4 | 5.5 | 1.6 | 3.2 |
| Conditioner C | 2.5 | 4.5 | 1.5 | 3.1 |
| Conditioner D | 2.4 | 5.0 | 1.5 | 4.5 |
| Conditioner E | 2.6 | 3.5 | 1.4 | 3.7 |
| Conditioner F | 2.3 | 5.0 | 1.5 | 4.5 |

Conditioner A to F correspond to base from table 10 with capsules A to F as described in example 1

The perfume intensity has been evaluated by the panel with all the capsules of the invention as being higher after rubbing than on fresh samples. The rubbing action is mechanically breaking the capsules that did deposit on the hair and remained even after rinsing. This result thus demonstrates the quality of the deposition. Furthermore, the olfactive performance of the invention's capsules in rinse-off hair conditioner consumer product was similar with a fresh prepared rinse-off hair conditioner base compared to a 3 months old rinse-off hair conditioner base therefore showing the stability of the capsules of the invention in the consumer product.

What is claimed is:

1. A process for the preparation of core-shell microcapsules comprising the following steps:
   a) dissolving at least one polyisocyanate having at least two isocyanate groups, in a perfume to form an oil phase;
   b) dispersing the oil phase obtained in step a) into an aqueous solution comprising an emulsifier to form an oil-in-water emulsion;
   c) adding, sequentially, to the oil-in-water emulsion obtained in step b) a polymeric cross-linker bearing amino groups with a molecular weight equal or higher than 2 000 g/mol chosen from the group consisting of a polyvinylamine, a polyethyleneimine, a polyaminoethylacrylate and mixtures thereof, followed by a polyamine with a molecular weight lower than 250 g/mol selected from the group consisting of 1,2-diaminopropane, 1,2-diaminoethane, diethylenetriamine, guanidine, water soluble guanidine salts, tris-(2-aminoethy)amine, N,N,N',N'-tetrakis(3-aminopropyl)-1,4-butanediamine, N,N'-bis(3-aminopropyl)-ethylenediamine, and 3,5-diamino-1,2,4-triazole, to form a microcapsule slurry.

2. The process according to claim 1, wherein the polymeric cross-linker bearing amino groups has a molecular weight that is either higher than 50 000 g/mol or higher than 200 000 g/mol.

3. The process according to claim 1, wherein the polymeric cross-linker bearing amino groups and the emulsifier are used in a weight ratio based on dry matter that is either between 0.1 and 10 or between 0.5 and 2.

4. The process according to claim 1, wherein at least one polyisocyanate is selected from the group consisting of a polyisocyanurate of toluene diisocyanate, a trimethylol propane-adduct of toluene diisocyanate, a trimethylol propane-adduct of xylylene diisocyanate, a trimer of hexamethylene diisocyanate, a trimer of isophorone diisocyanate, a trimethylol propane-adduct of hexamethylene diisocyanate, a biuret of hexamethylene diisocyanate and mixtures thereof.

5. The process according to claim 1, wherein the at least one polyisocyanate is used in an amount comprised between 2 and 20% by weight, relative to the total weight of the oil phase obtained in step a).

6. The process according to claim 1, wherein the emulsifier is selected from the group consisting of polyvinyl alcohol, a cellulose derivative, polyethylene oxide, a copolymer of polyethylene oxide and polyethylene or polypropylene oxide, a copolymer of acrylamide and acrylic acid, a copolymer of vinylpyrrolidone and a quaternized vinylimidazol, and sodium dodecyl sulfate.

7. The process according to claim 1, wherein the concentration of perfume is comprised between 10% and 60% by weight relative to the total weight of the microcapsule slurry.

8. The process according to claim 1 which further comprises recovering microcapsules from the microcapsule slurry.

9. The process according to claim 8, wherein the ratio between the average size of the microcapsules to the average droplet size of the emulsion obtained in step b) is comprised between 1.1 and 25 or between 1.1 and 10.

10. The process according to claim 8, which further comprises including the microcapsules in a perfuming composition comprising:

at least one ingredient selected from the group consisting of a perfumery carrier, a perfuming co-ingredient and mixtures thereof; and optionally, at least one perfumery adjuvant.

11. The process according to claim 8, which further comprises including the microcapsules in a perfuming consumer product as a perfuming ingredient.

12. The process according to claim 11, wherein the perfuming consumer product is provided in the form of a fine perfume, a cologne, an after-shave lotion, a liquid or solid detergent, a fabric softener, a fabric refresher, an ironing water, a paper, a bleach, a shampoo, a hair conditioner, a coloring preparation, a hair spray, a vanishing cream, a deodorant or antiperspirant, a perfumed soap, a shower or bath mousse, an oil or gel, a hygiene product, an air freshener, a "ready to use" powdered air freshener, a wipe, a dish detergent, a hard-surface detergent, an animal litter, a diaper, a sanitary napkin, a liner or a wipe.

13. The process according to claim 8, which further comprises including the microcapsules in a consumer product, wherein the microcapsules extend fragrance release of the perfume when the consumer product contacts a surface.

14. The process according to claim 13, wherein the consumer product is for skin, hair or fiber.

* * * * *